US00PP15560P3

(12) United States Plant Patent
Iwaki

(10) Patent No.: US PP15,560 P3
(45) Date of Patent: Feb. 15, 2005

(54) ***TORENIA* PLANT NAMED 'SUNRENILAHOPAS'**

(50) Latin Name: *Torenia hybrida*
Varietal Denomination: Sunrenilahopas

(75) Inventor: Kazunari Iwaki, Ohmihachiman (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 10/327,944

(22) Filed: Dec. 26, 2002

(65) Prior Publication Data

US 2004/0128722 P1 Jul. 1, 2004

(51) Int. Cl.[7] ..... A01H 5/00
(52) U.S. Cl. ..... Plt./263
(58) Field of Search ..... Plt./263

(56) References Cited

U.S. PATENT DOCUMENTS

| | | | |
|---|---|---|---|
| PP10,118 | P | 11/1997 | Miyazaki et al. |
| PP10,119 | P | 11/1997 | Nagase |
| PP10,120 | P | 11/1997 | Nagase |
| PP10,843 | P | 3/1999 | Tamura et al. |
| PP11,131 | P | 11/1999 | Miyazaki |
| PP12,105 | P2 | 9/2001 | Miyazaki |

*Primary Examiner*—Kent Bell
*Assistant Examiner*—Louanne Krawczewicz Myers
(74) *Attorney, Agent, or Firm*—Burns, Doane, Swecker & Mathis, LLP

(57) ABSTRACT

Disclosed herein is a *Torenia* plant having large flowers, yellowish-white petals with a yellow blotch and a red-purple floral tube. The plant has a semi-decumbent growth habit, medium branching and a great profusion of blooms. The entire plant remains in bloom for a considerable period of time. The plants grows and flowers well in shaded areas.

2 Drawing Sheets

Botanical/commercial classification: *Torenia hybrida*/*Torenia* Plant.
Varietal denomination: cv. 'Sunrenilahopas'.

BACKGROUND OF THE VARIETY

The *Torenia* is a very popular plant and is used for flower bedding and potting in the summer season. There are only a few varieties of the *Torenia* plants which have a semi-erect growth habit, medium branching, and a great profusion of blooms.

Accordingly, this invention is aimed at providing a new *Torenia* variety having large flowers, yellowish-white flower petals with a yellow blotch, a red-purple floral tube, a semi-erect growth habit, medium branching, and a great profusion of blooms.

The new variety of *torenia* plant according to this invention originated through the artificial chromosome doubling of the 'Sunrenihopas' variety (non-patented in the United States). During September 1998, cuttings of 'Sunrenihopas' variety were treated with 0.1% colchicines solution, and were propagated in a peat media by the use of cuttings at Yokaichi-shi, Shiga-ken, Japan. After two months, some surviving plantlets were transplanted into pots. In December 1998, colchiploids were obtained from the cultivation. The discovered *Torenia* plant from among these was propagated by the use of cuttings and was then grown in a bed and in pots where it was evaluated. The botanical characteristics of the plant were examined using the parent variety 'Sunrenihopas' variety and the similar 'Sunrenilapiho' variety (U.S. Plant Pat. No. 12,105) for comparison. As a result, it was concluded that this discovered *Torenia* plant is distinguishable from any other variety, whose existence is known to us.

Asexual propagation of the new variety at Aza-Iketani, Omori-cho, Yokaichi-shi, Shiga-ken, Japan, by the use of cuttings has confirmed that the new plant of the present invention is uniform and stable in its characteristics and reproduces true to type in succeeding generations.

The new variety of *Torenia* plant was named 'Sunrenilahopas'.

In the following description, the color-coding is in accordance with the R.H.S. Colour Chart of The Royal Horticultural Society, London, England (2001). A color chart based on The Japan Color Standard for Horticultural Plants (J.H.S. Color Chart) is also added for reference.

The botanical characteristics of the 'Sunrenihopas' variety parent are set forth hereafter.

Plant:
- *Growth habit.*—Semi-erect.
- *Plant height.*—Approximately 15 cm.

Stem:
- *Diameter.*—Approximately 2.2 mm.
- *Anthocyanin pigmentation.*—Present.
- *Branching.*—Medium.
- *Pubescence.*—Sparse.
- *Length of internode.*—Approximately 4.0 mm.

Leaf:
- *Shape of blade.*—Lanceolate.
- *Length.*—Approximately 2.5 cm.
- *Width.*—Approximately 1.7 cm.
- *Depth of incision.*—Medium.
- *Pubescence of upper side.*—Sparse.

Flower:
- *Diameter.*—Approximately 2.2 cm.
- *Height.*—Approximately 2.8 cm.
- *Color of floral tube.*—Bright reddish-purple (R.H.S. 78B, J.H.S. 8905).
- *Color of petal.*—Single color; white (R.H.S. 155D).
- *Yellow eye color.*—Present.
- *Calyx.*—Approximately 1.5 cm in length.

*Anthocyanin pigmentation of calyx.*—Present.
*Peduncle.*—Approximately 1.4 mm in thickness; and approximately 1.9 cm in length.
*Reproductive organs.*—1 pistil and 4 stamens.
*Flowering duration.*—Medium.

Physiological and ecological characteristics: Medium resistance to diseases and pests, and medium tolerances to heat and cold. The plant grows and has flowers in shaded areas.

The botanical characteristics of the 'Sunrenilapiho' variety are set forth hereafter.

Plant:
*Growth habit.*—Semi-erect.
*Plant height.*—Approximately 15 cm.

Stem:
*Diameter.*—Approximately 2.7 mm.
*Anthocyanin pigmentation.*—Present, and dark (R.H.S. 166A).
*Branching.*—Medium.
*Pubescence.*—Sparse.
*Length of internode.*—Approximately 5.5 cm.
*Color.*—Moderate yellow-green (R.H.S. 143C, J.H.S. 3709).

Leaf:
*Phyllotaxis.*—Opposite.
*Shape of blade.*—Lanceolate.
*Length.*—Approximately 3.8 cm.
*Width.*—Approximately 3.2 cm.
*Margin.*—Dentate.
*Color* (*upper side*).—R.H.S. 138A when immature and R.H.S. 137A when mature.
*Color* (*reverse side*).—R.H.S. 138B when immature and R.H.S. 137C when mature.
*Pubescence of upper side.*—Sparse.

Flower:
*Flower form.*—Globose.
*Diameter.*—Long (approximately 33 mm) across the flower face parallel to the horizontal plane.
*Height.*—Medium to long (approximately 35 mm).
*Color of floral tube.*—Vivid reddish-purple (R.H.S. 80A, J.H.S. 8906).
*Color of upper bilabiate petals.*—Pale purplish-white (R.H.S. 76D) on the upper surface and on the lower surface.
*Color of intermediate bilabiate petals.*—R.H.S. 80A in the center with white margins on the upper surface and R.H.S. 82A with white margins on the lower surface.
*Color of lowest bilabiate petals.*—R.H.S. 78B towards the base except for a white margin and white towards the tip on the upper surface and the lower surface.
*Color pattern of bilabiate petal.*—Bi-colored.
*Yellow eye color.*—Absent.
*Calyx.*—Medium (approximately 19 mm) in length.
*Anthocyanin pigmentation of calyx.*—Present towards the tip.
*Peduncle.*—1 medium (approximately 1.5 mm) in thickness; and medium (approximately 22 mm) in length.
*Reproductive organs.*—1 pistil and 4 stamens.
*Anther color.*—White.
*Flowering time.*—Late, early summer to mid-autumn.

Physiological and ecological characteristics: Moderate resistance to heat, cold, diseases and pests. Severe frost may be harmful to the plant. The resistance to powdery mildew is moderate.

SUMMARY OF THE NEW VARIETY

The new 'Sunrenilahopas' variety has a semi-erect habit, large flowers, yellowish-white flower petals with a yellow blotch and a red-purple floral tube, medium branching, and a great profusion of blooms.

BRIEF DESCRIPTION OF THE DRAWINGS

The accompanying photographs show, as nearly true as it is reasonably possible to make the same in color illustrations of this character, typical specimens of the new variety. The plants were approximately three months of age and were being grown in greenhouses at Yokaichi-shi, Shiga-ken, Japan.

DETAILED DESCRIPTION OF THE NEW VARIETY

Figure 1:
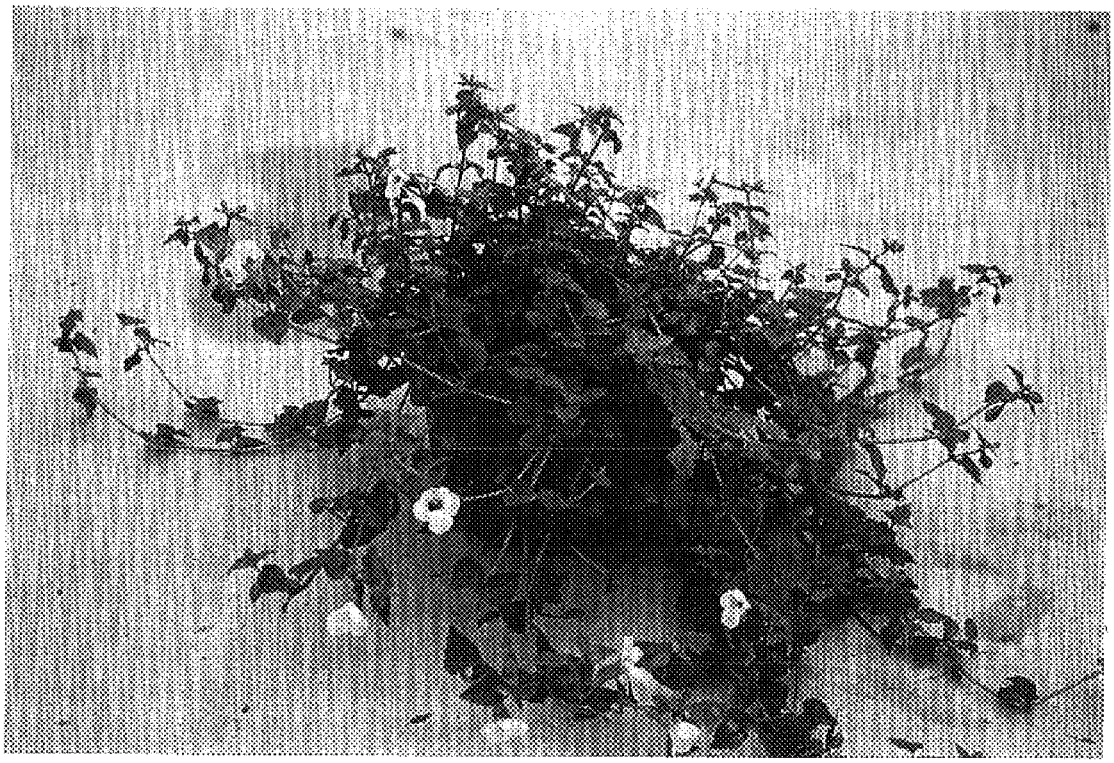
FIG. 1 is a photograph of a specimen of an entire plant of the new variety of the present invention while growing in a container.
Figure 2:
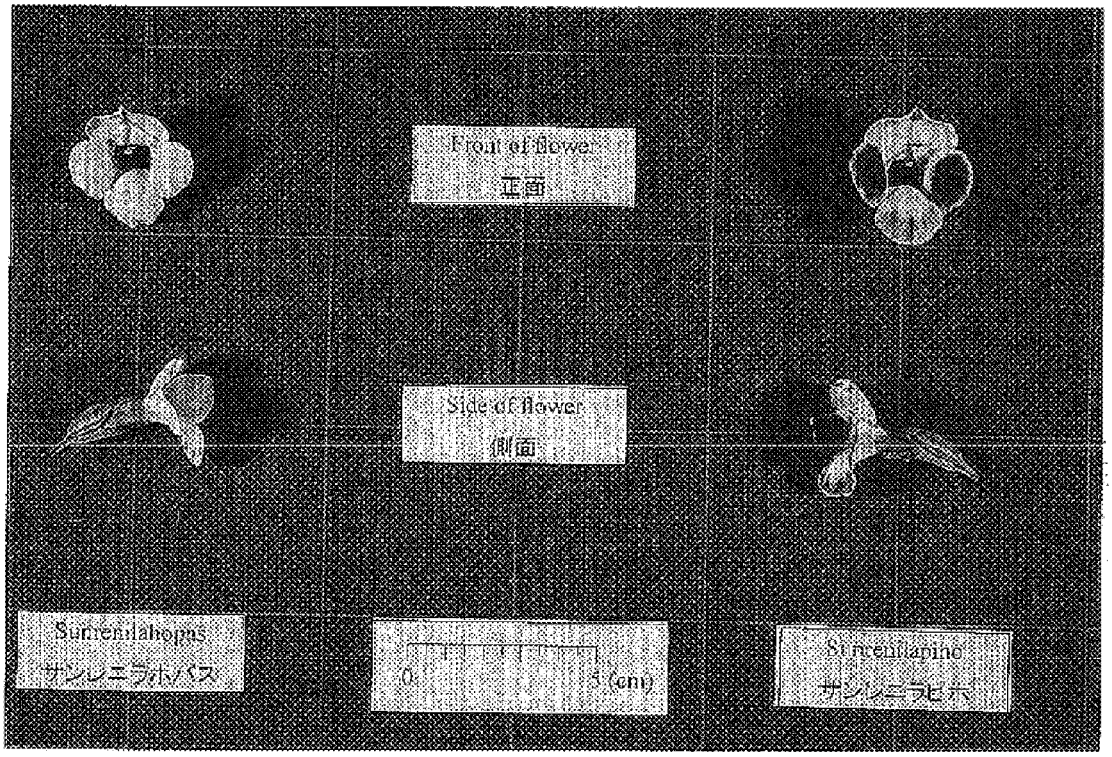
FIG. 2 is a photograph of specimens of flowers of the new variety of the present invention at the left and those of the 'Sunrenilapiho' variety for comparison at the right.

The botanical characteristics of the new and distinct 'Sunrenilahopas' variety of are set forth hereafter. The plants were observed during August at Yokaichi-shi, Shiga-ken, Japan while growing in 24 cm containers in a greenhouse. The plants had been propagated by the use of stem cuttings and were approximately three months of age.

Plant:
*Growth habit.*—Semi-erect.
*Plant height.*—Approximately 27 cm.
*Plant width.*—Approximately 70 cm.

Stem:
*Diameter.*—Approximately 2.0 mm.
*Length.*—Approximately 35 cm.
*Anthocyanin pigmentation.*—Near R.H.S. 60A.
*Branching.*—Medium.
*Pubescence.*—Sparse.
*Length of internode.*—Approximately 5.5 cm.
*Color.*—R.H.S. 144A.

Leaf:
*Shape of blade.*—Cordate.
*Apex.*—Acute.
*Base.*—Cordate.
*Margin.*—Serrate.
*Length.*—Approximately 2.5 cm.
*Width.*—Approximately 2.5 cm.
*Color* (*upper side*).—Dark green (R.H.S. 147A, J.H.S. 3716).
*Color* (*under side*).—R.H.S. 147B.
*Pubescence of upper side.*—Sparse.
*Thickness of petiole.*—Medium (Approximately 1.5 mm).
*Length of petiole.*—Short (Approximately 0.5 cm).

Flower:
*Inflorescence peduncles.*—Axillary.
*Peduncle color.*—R.H.S. 144A.
*Bud shape.*—Ellipsoidal.
*Bud length.*—Approximately 1.8 cm.
*Bud diameter.*—Approximately 1 cm.
*Bud texture.*—Pubescent.
*Bud color.*—R.H.S. 144B.
*Flowers on stem.*—Commonly 3.

*Bloom time.*—When planted in May outdoors, first blooms in June.

*Blooming frequency.*—Substantially continuously for approximately 6 months. Up to 150 or more blooms commonly are formed per plant.

*Fragrance.*—None.

*Flower form.*—Tubular and zygomorphic.

*Flower length.*—Medium (Approximately 30 mm).

*Flower width.*—Medium (Approximately 30 mm).

*Length of floral tube.*—Medium (approximately 30 mm).

*Color of floral tube.*—Dull red-purple (R.H.S. 70A, J.H.S.9215) on the outside and on the inside.

*Petal number.*—Four and fused.

*Petal shape.*—Elliptic.

*Petal length.*—Approximately 1.2 cm for the upper petal, approximately 1.5 cm for the side petals at the left and right, and approximately 1.5 cm for the lower petal.

*Petal width.*—Approximately 2.2 cm for the upper petal, approximately 1.2 cm for the side petals at the left and right, and approximately 1.5 cm for the lower petal.

*Petal apex.*—Rounded.

*Petal base.*—Fused.

*Petal margin.*—Entire and undulated.

*Color of petals.*—Single color; yellowish-white R.H.S. 155D on both surfaces.

*Yellow blotch on the lower petal.*—Present, and near R.H.S. 14D.

*Vertical line on the petals.*—Present.

*Wave of upper bilabiate petal.*—Weak.

*Calyx shape.*—Deeply two-lobed.

*Calyx; degree of development of wings.*—Medium.

*Calyx length.*—Short to medium (Approximately 18 mm).

*Calyx color.*—R.H.S. 144A on both surfaces.

*Anthocyanin pigmentation of calyx limb.*—Absent.

*Anthocyanin pigmentation of anther.*—Absent.

*Anther number.*—Two pairs of fused anthers.

*Anther size.*—The upper anthers commonly are approximately 3 mm in length and approximately 1 mm in width, and the lower anthers commonly are approximately 4 mm in length and approximately 1 mm in width.

*Anther color.*—The upper and the lower anthers are near R.H.S. 155B.

*Anther spur.*—Present.

*Filament color.*—Near R.H.S. 155B.

*Filament number.*—4.

*Filament length.*—The upper filaments commonly are approximately 3 mm in length, and the lower filaments commonly are approximately 10 mm.

*Pollen.*—Sparse abortive pollen is observed that is near R.H.S. 162D in coloration.

*Pistil number.*—1.

*Stigma size.*—Approximately 2 mm×1.5 mm.

*Style length.*—Approximately 1.8 cm.

*Style color.*—Near R.H.S. 76C.

*Ovary number.*—1.

*Ovary size.*—Approximately 1×7 mm.

*Ovary color.*—R.H.S. 177A.

*Fruit.*—None observed.

*Seeds.*—None observed.

*Peduncle thickness.*—Medium (Approximately 1.5 mm).

*Peduncle length.*—Short (Approximately 1.5 mm).

*Flowering longevity.*—Approximately 3 days on the plant.

*Hardiness.*—Susceptible to damage under 5° C.

Physiological and ecological characteristics: Moderate resistance to drought, diseases and pests, high tolerance to heat, and low tolerance to cold.

This new 'Sunrenilahopas' variety of *Torenia* plant is most suitable for growing in flower beds and pots, particularly in hanging baskets and in planters.

What is claimed is:

1. A new and distinct variety of *Torenia* plant, substantially as herein illustrated and described, characterized particularly as to novelty by (A) has a semidecumbent growth habit with medium branching, (B) forms large flowers with a great profusion of blooms and the entire plant remaining in bloom for considerable period of time, (C) displays flower petals that are yellowish-white with a yellow blotch and a red-purple floral tube, (D) displays moderate resistance to drought, diseases and pests and strong resistance to heat, and (E) grows and flowers well in shaded areas.

* * * * *